(12) United States Patent
Fahrenschon

(10) Patent No.: US 7,746,460 B2
(45) Date of Patent: Jun. 29, 2010

(54) DEVICE AND METHOD FOR SCANNING PIECES OF SOLID WOOD

(75) Inventor: Walter Fahrenschon, Weissenhorn (DE)

(73) Assignee: GreCon Dimter Holzoptimierung Süd GmbH & Co. KG, Illertissen (DE)

( * ) Notice: Subject to any disclaimer, the term of this patent is extended or adjusted under 35 U.S.C. 154(b) by 188 days.

(21) Appl. No.: 12/145,534

(22) Filed: Jun. 25, 2008

(65) Prior Publication Data

US 2008/0316473 A1 Dec. 25, 2008

(30) Foreign Application Priority Data

Jun. 25, 2007 (DE) .................. 10 2007 030 865

(51) Int. Cl.
*G01N 21/00* (2006.01)
(52) U.S. Cl. .................. 356/237.2; 356/237.1
(58) Field of Classification Search .............. 356/237.1, 356/237.2, 639
See application file for complete search history.

(56) References Cited

U.S. PATENT DOCUMENTS

| 5,644,392 | A | * | 7/1997 | Soest et al. ............... 356/237.1 |
| 6,631,006 | B2 | * | 10/2003 | Dick et al. .................. 356/625 |
| 6,756,789 | B1 | * | 6/2004 | Parker et al. ................. 324/637 |
| 2002/0171849 | A1 | * | 11/2002 | Dick et al. .................. 356/625 |
| 2005/0098004 | A1 | * | 5/2005 | Dick et al. ..................... 83/13 |
| 2006/0056659 | A1 | * | 3/2006 | Laurent et al. .............. 382/110 |

* cited by examiner

*Primary Examiner*—Roy Punnoose
(74) *Attorney, Agent, or Firm*—Gudrun E. Huckett

(57) ABSTRACT

A device for scanning pieces of solid wood has a pusher movable across a length of a piece of solid wood and at least one scanning unit mounted on the pusher. At least one side of the piece of solid wood is scanned by the at least one scanning unit as the at least one scanning unit moves together with the pusher. The at least one scanning unit has at least one camera with which the piece of solid wood is scanned. The at least one camera is adjustably mounted on the pusher.

19 Claims, 3 Drawing Sheets

DEVICE AND METHOD FOR SCANNING PIECES OF SOLID WOOD

BACKGROUND OF THE INVENTION

The invention relates to a device for scanning pieces of solid wood. The device comprises at least one scanning unit with which at least one side of the pieces of solid wood is scanned. The invention further relates to a method for scanning pieces of solid wood by means of the device as set forth above, wherein the pieces of solid wood are scanned on at least one side across the length of the pieces of solid wood with regard to flaws and quality of the wood.

In the lumber industry, scanning units are used for recognizing flaws in the wood and for determining the wood quality. The scanning unit inclusive illumination is arranged stationarily. The pieces of solid wood are individually transported by means of appropriate transportation devices through the scanning unit. The lead end and the trail end of a board are detected by means of suitable sensors and the length information in regard to the piece of solid wood is detected by means of transmitters. The thus determined board data are optimized to a cutting list according to which the piece of solid wood is sawed in the downstream sawing station in the form of a through feed saw. In other applications, the pieces of solid wood are transferred to a sorting station and sorted in accordance with the detected quality parameters.

Aside from through feed saws in which the pieces of solid wood are positioned and transported by means of feed rolls, chains, and toothed belts, push feed saws are also known in which the pieces of solid wood are positioned and transported by means of a pusher and a linear module.

SUMMARY OF THE INVENTION

It is an object of the present invention to configure a device of the aforementioned kind and a method of the aforementioned kind in such a way that the pieces of solid wood can be reliably scanned with a device having a simple configuration.

In accordance with the present invention, this is achieved in regard to the device in that the scanning unit is provided with a pusher that is movable across the length of the piece of solid wood to be scanned.

In accordance with the present invention, this is achieved in regard to the method in that the scanning unit is moved during the scanning process for detecting flaws/wood quality at least once across the length of the piece of solid wood.

With the device according to the invention, the scanning unit together with the pusher, with which the piece of solid wood is transported to the downstream sawing station, is moved across the length of the piece of solid wood that is then scanned by the scanning device as the scanning unit passes across the piece of solid wood. Because the pusher must be moved in any case for transporting the piece of solid wood into the sawing station or into the sorting station, the stroke to be performed by the pusher can be used at the same time for scanning the piece of solid wood.

Advantageously, the scanning unit has at least one camera for scanning the piece of solid wood. By means of the camera the piece of solid wood can be scanned properly.

In order for the scanning process to be performed quickly, the scanning unit has several cameras distributed about the circumference of the piece of solid wood. In this way, all sides of the piece of solid wood can be detected by means of the cameras in a single stroke movement of the pusher.

It is advantageously possible to provide each side of the piece of solid wood with a camera.

However, it is also possible that one camera simultaneously scans two sides of the piece of solid wood. For a piece of solid wood having a quadrangular cross-section only two cameras are therefore required that each scan two sides of the piece of solid wood. In this case, only one stroke of the pusher is required in order to scan all sides of the piece of solid wood across its length by means of the two cameras.

In another advantageous embodiment, the scanning unit has one camera and a mirror cooperating with the camera. The camera and the mirror are arranged relative to one another such that the camera itself scans two sides of the piece of solid wood and, by means of the mirror, the other two sides of the quadrangular cross-section of the piece of solid wood are scanned. In this way, by means of a single stroke of the pusher all sides of the piece of solid wood can be scanned across its length.

In order for the camera to be optimally adjusted for scanning, the camera is advantageously mounted on the pusher so as to be adjustable.

The mirror is also advantageously adjustably arranged on the pusher so that the mirror can also be adjusted relative to the piece of solid wood to be scanned.

During the scanning process the piece of solid wood is resting on supports.

According to another embodiment, the piece of solid wood is received between two rotating devices. In this connection advantageously at least one rotating device is driven in order to be able to rotate the piece of solid wood about its longitudinal axis.

At least one of the rotating devices is adjustable in the movement direction of the scanning unit in a direction toward the other rotating device. In this way, pieces of solid wood having different lengths can be received between the two rotating devices without any problem.

Advantageously, the scanning unit scans the piece of solid wood when the return stroke away from the sawing station is performed.

In another advantageous embodiments, the piece of solid wood that is at rest is scanned upon advancing stroke as well as return stroke of the scanning unit. During the two scanning steps, the solid piece of wood is at rest while the piece of solid wood is rotated about its longitudinal axis inbetween the two strokes.

DESCRIPTION OF THE PREFERRED EMBODIMENTS

Figure 1:
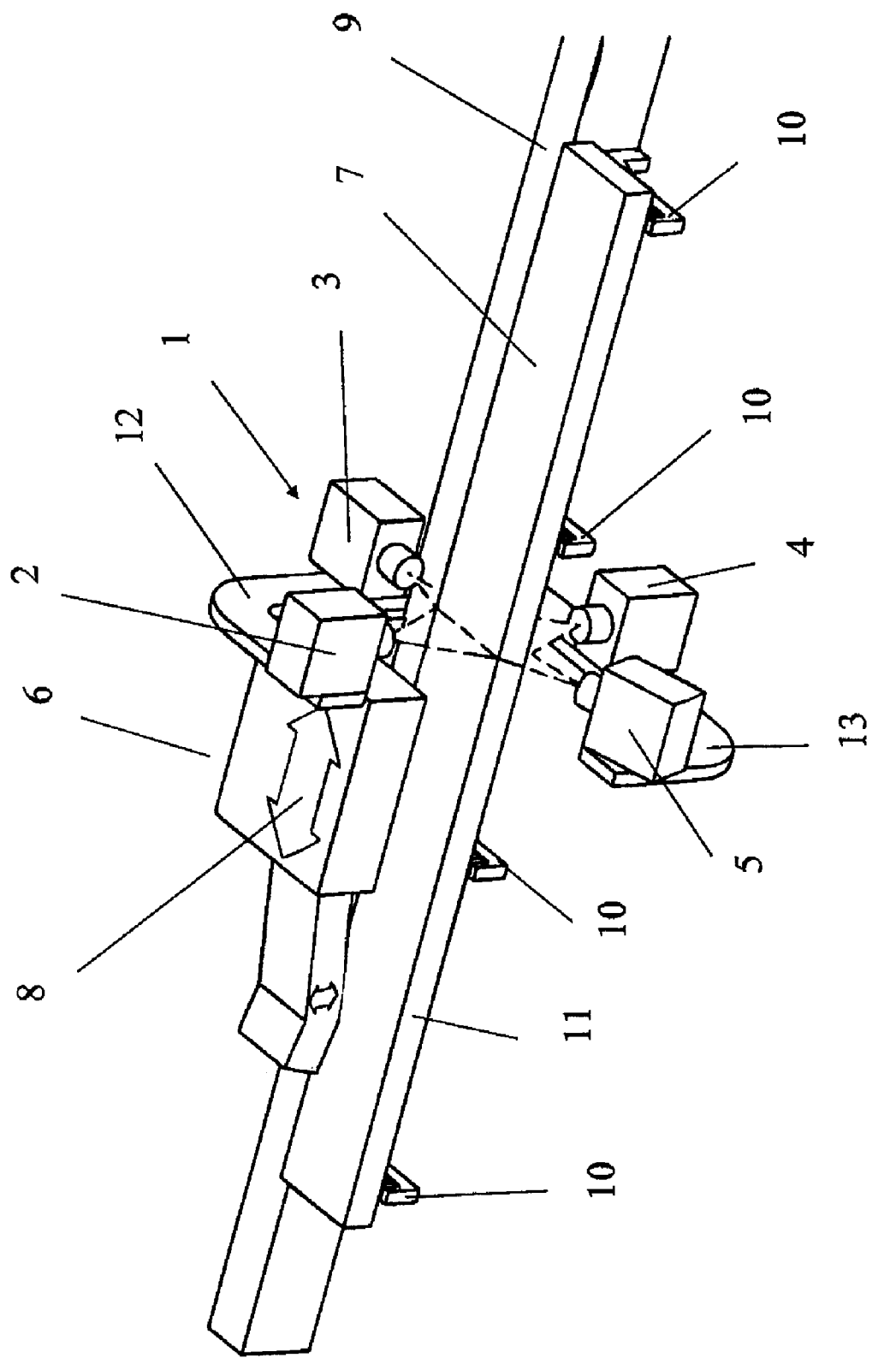
FIG. 1 is a perspective and simplified illustration of a first embodiment of the device according to the invention.

The device according to FIG. 1 with which flaws in the wood and the wood quality are to be determined, comprises a scanning unit 1 that is provided with four cameras 2 to 5 and an illumination means (not illustrated). The scanning unit 1 is mounted on a pusher 6 that is movable in the transport direction of the piece of solid wood 7 in the direction of arrow 8. The pusher 6 is movable along a guide 9; narrow supports 10 project transversely from the guide 9 and the piece of solid wood 7 to be scanned is resting on the supports 10. The supports 10 are arranged sequentially and are spaced apart from one another.

The cameras 2 to 5 are secured on at least one carrier 12 having a first arm 13 extending downwardly past the narrow side 11 of the piece of solid wood 7. The cameras 2 to 5 can be advantageously adjusted relative to the carrier 12 about axes that are positioned so as to extend in the travel direction 8. In this way, the cameras 2 to 5 can be adjusted optimally to the piece of solid wood to be scanned.

In the position illustrated in FIG. 1, the piece of solid wood 7 is located in the feeding station for being supplied to the downstream sawing step. By means of the pusher 6 the preceding piece of solid wood 7 has already been transported to the saw. When performing the return stroke, the pusher 6 moves along the piece of solid wood positioned within the feeding station. The cameras 2 to 5 record the data of the piece of solid wood (board) 7 and the data are subsequently optimized in a cutting list. The cameras 2 to 5 are positionally adjusted on the carrier 12 in such a way that all four sides of the piece of solid wood can be scanned. In the embodiment, the piece of solid wood 7 is a flat board. The cameras 2, 4 are positioned at a spacing above and below the piece of solid wood 7 and scan upon return stroke of the pusher 6 the top and bottom sides. The two cameras 3, 5 are located at a spacing adjacent to the piece of solid wood 7 and scan the two narrow sides. When the return stroke is performed, the cameras 2 to 5 will record flaws. Moreover, the wood quality is determined by means of the cameras. Also, the length of the piece of solid wood 7 can be determined by means of the scanning unit 1. These pieces of information provide the board data that are then optimized to a cutting list. The cutting list is supplied, as is known in the art, to the downstream sawing unit that, based on the data of the cutting list, will saw the piece of solid wood. As soon as the pusher 6 upon return stroke has passed the piece of solid wood 7, its travel direction is reversed. It will now entrain the piece of solid wood 7 that has been previously scanned and will feed it to the saw. In the meantime, in the feeding station the next piece of solid wood 7 is placed onto the supports 10 and, upon return stroke of the pusher 6, will be scanned by the scanning unit 1 in the way described. In this way, the pieces of solid wood to be transported to the sawing station or saw are scanned sequentially by means of the scanning unit 1 when the pusher 6 performs the return stroke.

Figure 2:
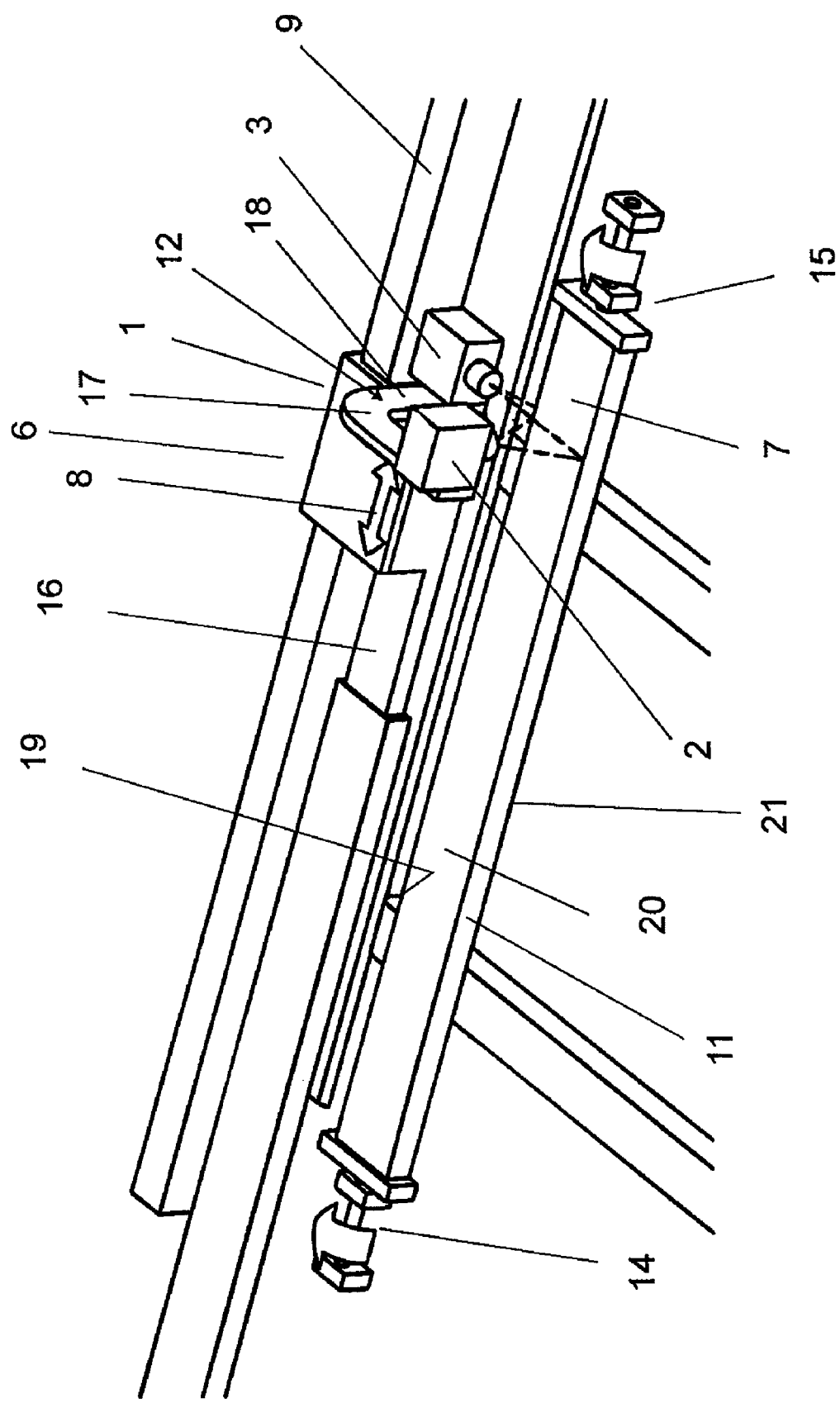
FIG. 2 shows in a perspective and simplified illustration a further embodiment of the device according to the invention.

In the embodiment according to FIG. 2 the board-shaped piece of solid wood 7 is in a ready position upstream of the feeding position. The piece of solid wood 7 is positioned in accordance with the preceding embodiment parallel to the travel direction 8 of the pusher 6. The piece of solid wood 7 is secured at both ends by a rotating device 14, 15, respectively, whose axis of rotation extends parallel to the travel direction 8 of the pusher 6. The pusher 6 is seated on the free end of an arm 16 and is supported on the guide 9. The pusher 6 comprises the carrier 12 on which two cameras 2, 3 are secured. In accordance with the preceding embodiment, the carrier 12 is L-shaped wherein the camera 2 is arranged at the free end of arm 17 and the camera 3 on the free end of the other arm 18 of the L-shaped carrier 12. The support arm 17 extends transversely to the travel direction 8 across the piece of solid wood 7. In this way, the camera 2 will scan the top side 20 of the piece of solid wood facing the camera. The camera 3 that is supported on the support arm 18 extending downwardly is arranged such that it will detect the narrow side 19 of the piece of solid wood 7 facing the pusher 6. The two cameras 2, 3, or only one of them, are advantageously pivotably supported on the carrier 12 about an axis that extends in the travel direction 8 so that the cameras 2, 3 can be optimally adjusted relative to the piece of solid wood to be scanned.

The pusher 6 is positioned at the beginning of the scanning process in the area behind the piece of solid wood 7. From this position, the pusher 6 is moved together with the scanning unit 1 in FIG. 2 to the right wherein the two cameras 2, 3 scan the top side 20 and the narrow side 19 of the piece of solid wood 7. During this stroke of the pusher 6, the preceding piece of solid wood is sawed at the same time in the sawing station. As soon as the scanning unit 1 has scanned the narrow side 19 and the top side 20, the piece of solid wood 7 is rotated by means of the two rotating devices 14, 15 about its longitudinal axis by 180 degrees. Now the pusher 6 with the scanning unit 1 is returned. The cameras 2, 3 scan the bottom side 21 that is now positioned on top and the narrow side 11 of the piece of solid wood 7. The data of the board that have been recorded during the advance stroke and the return stroke are optimized to a cutting list that is transmitted to the downstream sawing station. By means of the pusher 6, the piece of solid wood 7 is subsequently transported to the sawing station. After transfer of the board into the sawing station, the next piece of solid wood 7 is advantageously clamped in the rotating devices 14 15. At least one of the two rotating devices 14,15 is adjustable in the travel direction 8 so that by means of the two rotating devices 14, 15 pieces of solid wood 7 having different lengths can be clamped.

Figure 3:
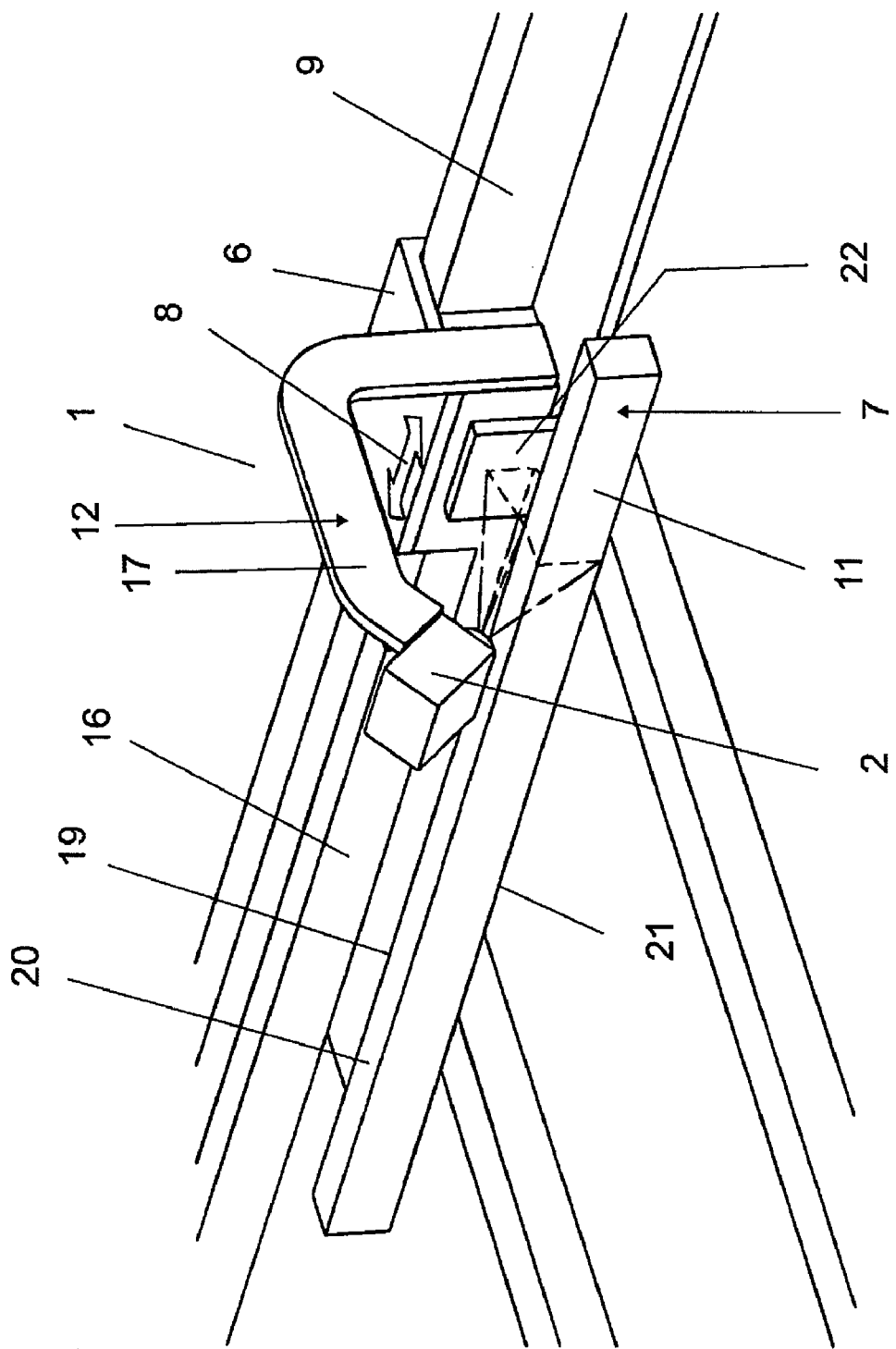
FIG. 3 shows in a perspective and simplified illustration yet another embodiment of the device according to the invention.

In the embodiment according to FIG. 3, the piece of solid wood is in a ready position upstream of the feeding position. In contrast to the preceding embodiments, the piece of solid wood 7 is no longer a board but a beam. The pusher 6 is provided with a scanning unit 1 and supported on the guide 9. The pusher 6 is moved by means of the arm 16 in the travel direction 8. The scanning unit 1 has an L-shaped carrier 12. On the free end of the top arm 17 there is camera 2 that is located in the area above and adjacent to the piece of solid wood 7. The camera 2 is adjusted such that it will scan the side 11 as well as the top side 20 of the piece of solid wood 7. The camera 2 for this purpose is positioned at a slant, for example, at an angle of 450 relative to the vertical. It is advantageous when the slant angle of the camera 2 can be adjusted. In this case, the camera 2 is pivotably supported on the carrier 12 so that it can be adjusted optimally.

On the pusher 6 there is also at least one mirror 22 that is arranged such that the camera 2 can scan by means of the mirror 22 also the side 19 and the bottom side 21 of the piece of solid wood 7. The mirror 22 is advantageously arranged on the pusher 6 to as to be height-adjustable and/or adjustable with regard to its slant.

With this device, the scanning process is either carried out on advancing stroke of the pusher 6 or on return stroke. By means of the single camera 2 in connection with the mirror 22 all four sides of the piece of solid wood 7 can be scanned. Accordingly, the board data are recorded and optimized to a cutting list based on which the piece of solid wood 7 is sawed in the downstream sawing station.

The cameras provided in the different devices can, of course, be arranged in different numbers and arrangement on the pusher 6 in deviation from the embodiments disclosed and explained in connection with the FIGS. 1 to 3. Since the scanning unit 1 moves together with the pusher 6, a simple and still reliable recognition of flaws and wood quality is realized.

The specification incorporates by reference the entire disclosure of German priority document 10 2007 030 865.7 having a filing date of Jun. 25, 2007.

While specific embodiments of the invention have been shown and described in detail to illustrate the inventive principles, it will be understood that the invention may be embodied otherwise without departing from such principles.

What is claimed is:

1. A device for scanning pieces of solid wood, the device comprising:
a pusher movable across a length of a piece of solid wood;
at least one scanning unit mounted on the pusher, wherein the at least one scanning unit scans at least one side of the piece of solid wood.

2. The device according to claim 1, wherein the at least one scanning unit comprises at least one camera with which the piece of solid wood is scanned.

3. The device according to claim 2, wherein the at least one camera is adjustably mounted on the pusher.

4. The device according to claim 1, wherein the at least one scanning unit comprises several cameras distributed about a circumference of the piece of solid wood with which cameras the piece of solid wood is scanned.

5. The device according to claim 4, wherein the cameras are adjustably mounted on the pusher.

6. The device according to claim 4, wherein the cameras each are assigned to one side of the piece of solid wood, respectively.

7. The device according to claim 4, wherein the cameras each are assigned to two sides of the piece of solid wood, respectively.

8. The device according to claim 1, wherein the at least one scanning unit comprises one camera and at least one mirror cooperating with the camera for detecting all four sides of the piece of solid wood.

9. The device according to claim 8, wherein the camera is adjustably mounted on the pusher.

10. The device according to claim 8, wherein the camera scans two of four sides of the piece of solid wood and the at least one mirror scans the other two of the four sides.

11. The device according to claim 8, wherein the at least one mirror is adjustably arranged on the pusher.

12. The device according to claim 1, comprising supports on which the piece of solid wood is resting.

13. The device according to claim 1, comprising two rotating devices between which the piece of solid wood is clamped.

14. The device according to claim 13, wherein at least one of the rotating devices is driven.

15. The device according to claim 13, wherein at least one of the rotating devices is adjustable in a travel direction of the scanning unit.

16. A method for scanning pieces of solid wood with a device comprising a pusher movable across a length of a piece of solid wood and at least one scanning unit mounted on the pusher, the method comprising the step of:
moving the at least one scanning unit at least once across a length the piece of solid wood for detecting flaws and wood quality of the piece of solid wood.

17. The method according to claim 16, further comprising the step of keeping at rest the piece of solid wood while moving the at least one scanning unit.

18. The method according to claim 16, wherein the step of moving is a return stroke of the at least one scanning unit away from a sawing station.

19. The method according to claim 16, wherein the step of moving comprises an advancing stroke toward a sawing station and a return stroke away from the sawing station, wherein the piece of solid wood is at rest during the advancing and return strokes, further comprising the step of rotating the piece of solid wood about a longitudinal axis of the piece of solid wood between the advancing and return strokes.

* * * * *